Figure 1A:
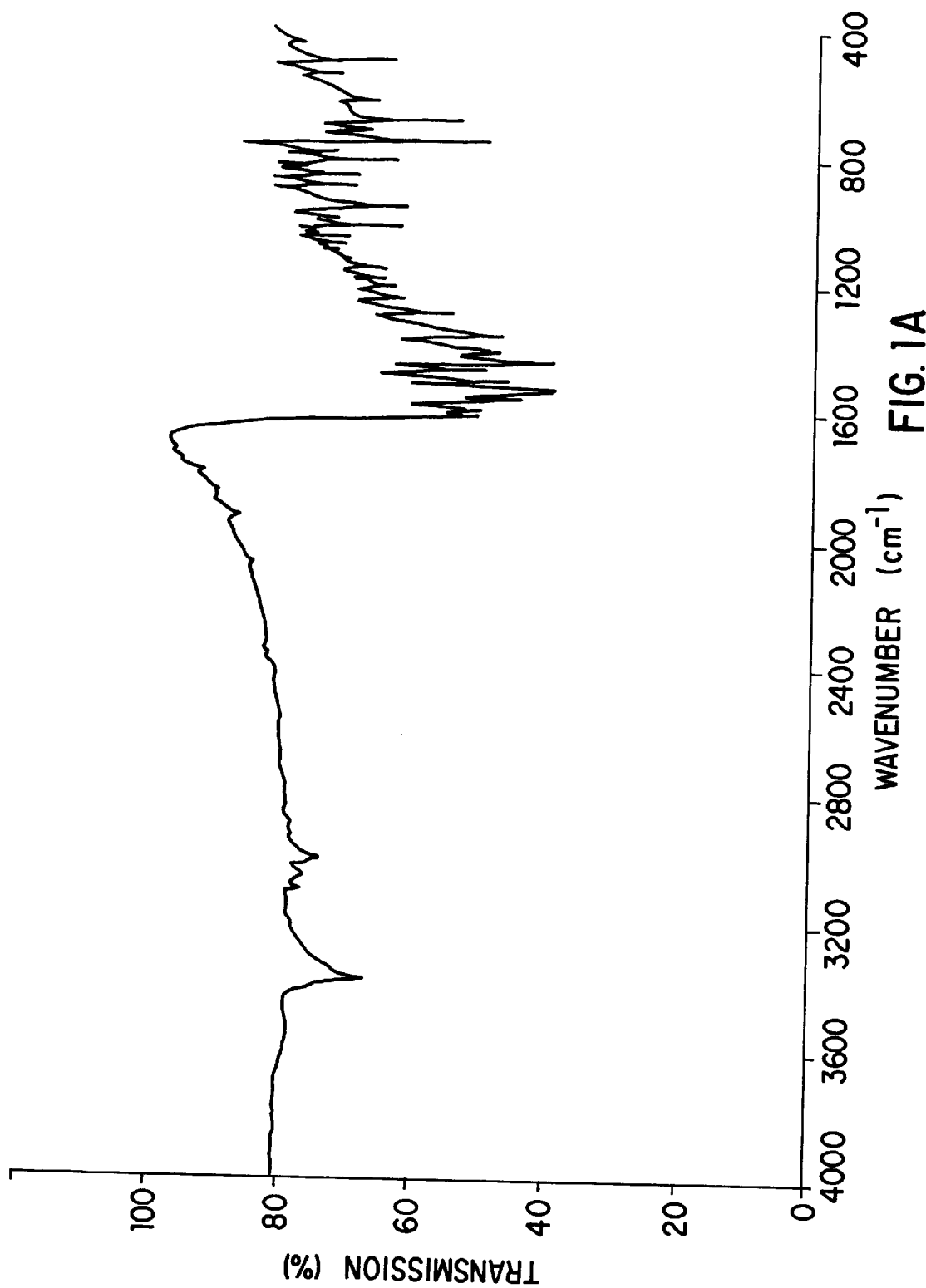

United States Patent [19]

Baettig et al.

[11] Patent Number: 5,830,899
[45] Date of Patent: Nov. 3, 1998

[54] CRYSTAL MODIFICATION OF (4-CYCLOPROPYL-6-METHYL-PYRIMIDIN-2-YL)PHENYL-AMINE

[75] Inventors: Willy Baettig, Pratteln; Reinhard Georg Hanreich, Basel, both of Switzerland

[73] Assignee: Novartis Corporation, Summit, N.J.

[21] Appl. No.: 909,491

[22] Filed: Aug. 12, 1997

Related U.S. Application Data

[63] Continuation of Ser. No. 692,303, Aug. 5, 1996, abandoned, which is a continuation of Ser. No. 330,274, Oct. 27, 1994, abandoned.

[30] Foreign Application Priority Data

Nov. 9, 1993 [CH] Switzerland ............... 3368/93
Jul. 28, 1994 [CH] Switzerland ............... 2393/94

[51] Int. Cl.$^6$ .................. A61K 31/505; C07D 239/42
[52] U.S. Cl. ................. 514/275; 544/330; 544/332
[58] Field of Search ................. 514/275; 544/330, 544/332

[56] References Cited

U.S. PATENT DOCUMENTS 4,997,941  3/1991  Hubele .................. 544/332
5,153,200  10/1992  Hubele .................. 514/275

FOREIGN PATENT DOCUMENTS

A-310550  4/1989  European Pat. Off. .

OTHER PUBLICATIONS

CIPAC Handbook, vol. 1, Analysis of Technical and Formulated Pesticides, 1970, pp. 860–869 and 980–983.

Phytoma, No. 458, p. 53, Feb. 1994.

Crop Protection, vol. 13, p. 541 (1994).

Pesticide Science, vol. 42, p. 163 (1994).

*Primary Examiner*—Yogendra N. Gupta
*Attorney, Agent, or Firm*—Hesna J. Pfeiffer

[57] ABSTRACT

Unlike (4-cyclopropyl-6-methyl-pyrimidin-2-yl)-phenyl-amine of the known crystal modification A, (4-cyclopropyl-6-methyl-pyrimidin-2-yl)-phenyl-amine of crystal modification B of high eutectic purity (content at least 98%) and having a melting point of from 73° C. to 75° C., as a fungicidal active ingredient in plant-protection compositions, does not have a tendency to crystal growth. Such compositions have a high degree of storage stability and retain their original good suspensibility and dispersibility.

17 Claims, 2 Drawing Sheets

CRYSTAL MODIFICATION OF (4-CYCLOPROPYL-6-METHYL-PYRIMIDIN-2-YL)PHENYL-AMINE

This is a Continuation of Ser. No. 08/692,303, filed Aug. 5, 1996, abandoned, which is a Continuation of Ser. No. 08/330,274, filed Oct. 27, 1994, abandoned.

The present invention relates to (4-cyclopropyl-6-methyl-pyrimidin-2-yl)-phenyl-amine of crystal modification B having a melting point higher than 73° C., preferably from 73° to 75° C., to a process for the preparation of that crystal modification, to a composition comprising that crystal modification, and to the use thereof in the control of fungus infestation in cultivated plants.

EP-A-0 310 550 discloses (4cyclopropyl-6-methyl-pyrimidin-2-yl)-phenyl-amine of crystal modification A having a melting point of from 67° C. to 69° C. That fungicide is effective against a number of diseases caused by ascomycetes or deuteromycetes. Solid formulations of that active ingredient have, however, only limited storage stability, which manifests itself especially in undesired crystal growth. The result in practice is, for example, that the spray mixture prepared for application is not sufficiently suspensible or dispersible and thus causes blockage of the spray nozzles.

Figure 1B:
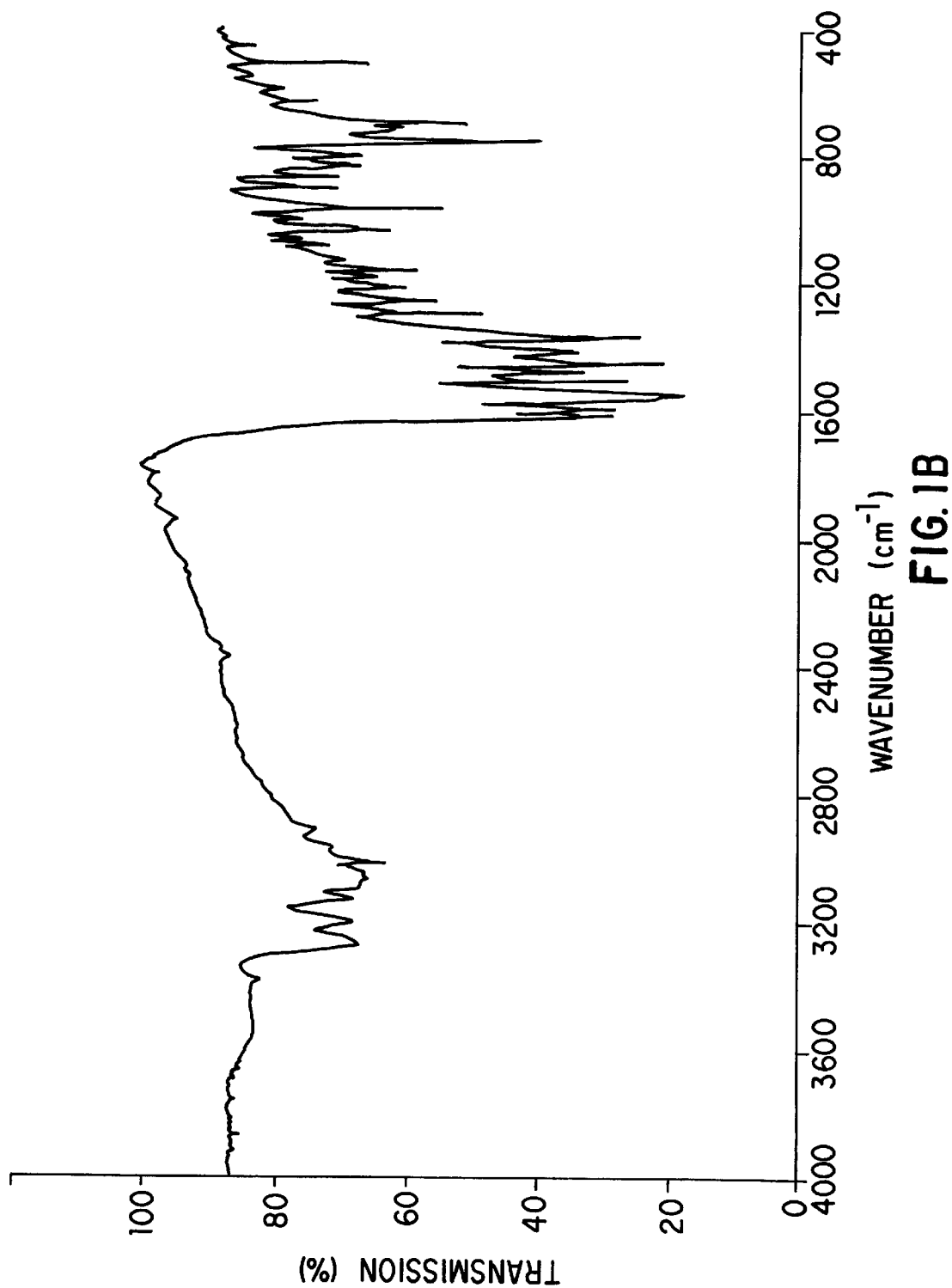

It has now been found, surprisingly, that by suitable selection of the crystallisation process for (4-cyclopropyl-6-methyl-pyrimidin-2-yl)-phenyl-amine, a novel crystal modification B can be prepared which does not have those undesired properties. The novel crystal modification B has a melting point of from 73° C. to 75° C. and differs both in its X-ray powder diagram (see Table 1) and in its IR spectrum from crystal modification A, which has a lower melting point (see IR spectra FIGS. 1A and 1B). Crystal modification B according to the invention thus differs in a characteristic manner from crystal modification A in its melting point, IR spectrum and X-ray powder diagram.

TABLE 1

X-ray powder diagram. Recorded using a Guinier camera (FR 552 from Enraf-Nonius) in transmission geometry using quartz as internal standard and using copper-K$\alpha_1$ irradiation ($\lambda$ = 1.54060 Å) on X-ray film.

| Crystal modification A | | Crystal modification B | |
|---|---|---|---|
| d-value (Å) | Intensity | d-value (Å) | Intensity |
| 13.0 | medium | 12.9 | medium |
| 7.8 | medium | 8.7 | strong |
| 6.6 | medium | 6.8 | strong |
| 6.5 | weak | 6.1 | weak |
| 5.74 | very weak | 5.93 | very weak |
| 5.06 | very strong | 5.66 | strong |
| 4.90 | weak | 5.39 | weak |
| 4.81 | strong | 5.19 | very weak |
| 4.49 | very weak | 4.96 | weak |
| 4.39 | weak | 4.81 | medium |
| 4.11 | medium | 4.75 | medium |
| 3.93 | medium | 4.55 | very strong |
| 3.89 | strong | 4.47 | medium |
| 3.60 | weak | 4.36 | weak |
| 3.54 | very strong | 3.97 | weak |
| 3.34 | strong | 3.86 | mediurn |
| 3.30 | weak | 3.80 | very strong |
| 3.22 | very weak | 3.78 | medium |
| 3.16 | weak | 3.67 | medium |
| 3.12 | very weak | 3.56 | medium |
| | | 3.54 | very weak |
| | | 3.42 | medium |
| | | 3.38 | weak |

TABLE 1-continued

X-ray powder diagram. Recorded using a Guinier camera (FR 552 from Enraf-Nonius) in transmission geometry using quartz as internal standard and using copper-K$\alpha_1$ irradiation ($\lambda$ = 1.54060 Å) on X-ray film.

| Crystal modification A | | Crystal modification B | |
|---|---|---|---|
| d-value (Å) | Intensity | d-value (Å) | Intensity |
| | | 3.30 | medium |
| | | 3.25 | very weak |
| | | 3.16 | weak |
| | | 3.09 | weak |
| | | 3.04 | very weak |

Solid formulations comprising the novel crystal modification B have the distinct advantage over formulations comprising the known modification A that they have a high degree of storage stability and retain their outstanding physico-chemical properties, such as their suspensibility and dispersibility, after long storage periods, even at elevated temperatures.

Thermodynamic tests have shown that crystalline (4-cyclopropyl-6-methyl-pyrimidin-2-yl)-phenyl-amine of crystal modification A can be completely converted into the novel crystal modification B within a few hours in the presence of a solubiliser (for example an organic solvent such as toluene or methylcyclohexane) at a temperature in the region of 26° C. Below that temperature, albeit after a substantially longer period of time, quantitative conversion of crystal modification B to A takes place. That conversion process does not, however, play any role in agrochemical applications.

In the absence of a solubiliser, crystal modification A can be converted at a temperature just below its melting point of from 67° to 69° C. into modification B, which has a higher melting point. That process is observed especially during grinding in a mechanical mill.

Surprising, on the other hand, is the finding that, in the absence of a solubiliser, there is no detectable conversion from modification B to modification A, which is of very great importance for practical purposes. It means that storage-stable formulations of modification B can be made that do not convert into those of modification A even at relatively low temperatures, for example close to freezing point.

Experiments with saturated solutions of the two modifications have produced the following interrelationships:

Experimental conditions: A saturated solution of (4-cyclopropyl-6-methyl-pyrimidin-2-yl)-phenyl-amine in toluene is prepared, followed by 2–3 hours' stirring and inoculation with about 20 mg of compound. Stirring is continued for 2–3 hours and then the solid is filtered off. The crystals are dried in vacuo at the appropriate temperature. The modification of the dry crystals is determined by DSC measurement (melting point).

| Temperature [°C.] | Starting condition: saturated solution with solids of crystal modification A at the bottom | Starting condition: saturated solution with solids of crystal modification B at the bottom |
|---|---|---|
| 20 | A + inoculation with A→A<br>A + inoculation with B→A | B + inoculation with A→A<br>B + inoculation with B→A |
| 26 | A + inoculation with A→A | B + inoculation with A→A/B |

-continued

| Temperature [°C.] | Starting condition: saturated solution with solids of crystal modification A at the bottom | Starting condition: saturated solution with solids of crystal modification B at the bottom |
|---|---|---|
| 30 | A + inoculation with B→A | B + inoculation with A→B |
| 35 | A + inoculation with B→B | B + inoculation with A→B |

For application in practice, therefore, the presence of as high a proportion of modification B as possible is important in order to prevent further conversion of crystals from A→B during storage or application (blockage of spray nozzles or formation of lumps in the formulated product).

The present invention relates to (4-cyclopropyl-6-methyl-pyrimidin-2-yl)-phenyl-amine of crystal modification B of high eutectic purity (content at least 98%), having a melting point higher than 73° C., preferably from 73° C. to 75° C., an IR spectrum according to FIG. 1.2 having a characteristic NH band at 3200–3300 cm$^{-1}$ (st=stretching vibration) and an X-ray powder diagram using copper-K$\alpha_1$ radiation having the data according to Table 1.

It should be noted that rapid heating of a sample of modification B can lead to an apparent point of from 74.5° to 76° C. It is nevertheless the same crystalline B modification.

The present invention relates also to a process for the large-scale preparation of (4-cyclo-propyl-6-methyl-pyrimidin-2-yl)-phenyl-amine of crystal modification B, wherein that compound is prepared by melt-crystallisation.

Chemical processes for the preparation of (4-cyclopropyl-6-methyl-pyrimidin-2-yl)-phenyl-amine are described in EP-A-0 310 550. For the novel crystal modification B, however, the active ingredient is crystallised from a suitable solvent (for example isopropanol, methylcyclohexane) or obtained in the form of a crude melt by distilling off the solvent. In order to achieve the requisite purity, the crude melt is subsequently distilled using a thin-layer evaporator. Both qualities of active ingredient (from the crystallisation process and from the melt process) are suitable for yielding by the melt-crystallisation process the desired crystal modification B of high eutectic purity. In that process, the hot product melt is cooled in a suitable apparatus to from 72° to 75° C., preferably 74° C. In a special form of the process, the crystals that form are scraped off the cooled kettle wall. It has proved very advantageous for the kettle wall to be at a temperature of from 40° C. to 60° C., especially 50° C. The melt thus obtained, which now contains seed crystals, is cooled further to complete the crystallization process. The melt is advantageously passed by means of a suitable apparatus to a cooled surface (for example a flake-forming roller or flake-forming belt) until the crystallisation is complete.

The present invention relates also to a composition that comprises as active ingredient (4-cyclopropyl-6-methyl-pyrimidin-2-yl)-phenyl-amine of crystal modification B having a melting point higher than 73° C., preferably from 73° to 75° C., and a suitable carrier. In a special form of the present invention the composition can also comprise further fungicides, bactericides, selective herbicides and insecticides, nematicides, molluscicides or mixtures of several of those active ingredients. The invention relates also to such fungicidal mixtures or compositions.

The present invention also includes the preparation of those compositions, which comprises intimately mixing the active ingredient with one or more carriers and, if desired, another active ingredient. Also included is a method of treating plants, which comprises the application of a fungicidally effective amount of (4cyclopropyl-6-methyl-pyrimidin-2-yl)-phenyl-amine of crystal modification B or of the novel composition.

(4-Cyclopropyl-6-methyl-pyrimidin-2-yl)-phenyl-amine of crystal modification B can be used in unmodified form, i.e. as obtained from the preparation process, but it is preferably formulated in customary manner with the adjuvants customary in formulation technology, for example suspensions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising (4-cyclo-propyl-6-methyl-pyrimidin-2-yl)-phenyl-amine of crystal modification B having a melting point of from 73° C. to 75° C., can be prepared in known manner, for example by intimately mixing and/or grinding the active ingredients with the carrier or carriers.

Carriers within the scope of the present invention can be solid or liquid. The solid carriers used, e.g. for dusts and dispersible powders, are normally natural mineral fillers, such as calcite, talcum, kaolin, montinorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Examples of liquid carriers are solvents and surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

Suitable surface-active compounds are non-ionic, cationic and/or anionic surfactants having good emulsifying, dispersing and wetting properties. The term surfactant is to be understood as including mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which can be used in the compositions according to the invention, are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Surfactant Handbook), Carl Hanser Verlag, Munich/Vienna 1981.

The fungicidal compositions usually comprise 0.1 to 99% (w/w), preferably 0.1 to 95% (w/w), of (4-cyclopropyl-6-methyl-pyrimidin-2-yl)-phenyl-amine of crystal modification B, 1 to 99% (w/w) of a solid or liquid adjuvant, and 0 to 25% (w/w), preferably 0.1 to 25% (w/w), of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), anti-foams, e.g. silicone oil, preservatives, viscosity regulators, binders and tackifiers, as well as fertilisers or other active ingredients for obtaining special effects. Those other active ingredients may be micronutrient donors or other compositions that influence plant growth.

Preferred formulations have especially the following composition (throughout, percentages are by weight)

| Dusts: | |
|---|---|
| active ingredient: | 0.1 to 50%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

(4Cyclopropyl-6-methyl-pyrimidin-2-yl)-phenyl-amine according to the invention is generally used successfully at rates of application of from 0.001 to 2 kg/ha, especially from 0.005 to 1 kg/ha. The concentration required to achieve the desired effect can be determined by experiment. It is dependent upon the type of action, the stage of development of the cultivated plant and the risk of attack by the disease, and also upon the application (place, time, method) and, in dependence on those parameters, can vary within wide limits.

(4Cyclopropyl-6-methyl-pyrimidin-2-yl)-phenyl-amine of crystal modification B according to the invention is customarily used in the form of a composition and can be applied to the area or plant to be treated simultaneously with or in succession with other active ingredients.

A preferred method of applying (4cyclopropyl-6-methyl-pyrimidin-2-yl)-phenyl-amine of crystal modification B according to the invention or an agrochemical composition comprising that active ingredient is application to the foliage of the plants (foliar application), the number of applications and the rate of application depending on the risk of infestation by the organism in question. However, crystal modification B according to the invention can also penetrate the plants through the roots via the soil (systemic action) if the locus of the plants is impregnated with a liquid formulation or if the active ingredient is incorporated in solid form into the soil, e.g. in granular form (soil application). In paddy rice crops, such granules may be applied in metered amounts to the flooded rice field. (4Cyclopropyl-6-methyl-pyrimidin-2-yl)-phenyl-amine of crystal modification B according to the invention can, however, also be applied to grains (=seed) (coating), either by impregnating the grains with a liquid formulation or by coating them with a solid formulation. A further advantageous method of application is the controlled release of active ingredient. For that purpose a solution of the active ingredient is applied to granulated mineral carriers or polymerised granules (urea/formaldehyde) and allowed to dry. If desired, it is also possible additionally to apply a coating (coated granules) that allows the active ingredient to be released in metered amounts over a specific period of time. The granules are then applied in known manner.

(4Cyclopropyl-6-methyl-pyrimidin-2-yl)-phenyl-amine of crystal modification B according to the invention has a biocidal spectrum for controlling fungus infestation that is very advantageous from the point of view of practical requirements. It has very advantageous curative, preventive and, especially, systemic properties and is used to protect a large number of cultivated plants. It can be used to inhibit or destroy the pests occurring on plants or parts of plants (fruit, blossom, leaves, stalks, tubers, roots) of different crops of useful plants, while parts of the plants that grow later are also protected, for example against phytopathogenic micro-organisms.

(4Cyclopropyl-6-methyl-pyrimidin-2-yl)-phenyl-amine according to the invention is effective, for example, against the phytopathogenic fungi belonging to the following classes: *Fungi imperfecti* (especially Botrytis, and also Pyricularia, Helminthosporium, Fusarium, Septoria, Cercospora and Alternaria); Basidiomycetes (e.g. Rhizoctonia, Hemileia, Puccinia). It is also effective against the class of the Ascomycetes (e.g. Venturia and Erysiphe, Podosphaera, Monilinia, Uncinula) and the Oomycetes (e.g. Phytophthora, Pythium, Plasmopara).

(4Cyclopropyl-6-methyl-pyrimidin-2-yl)-phenyl-amine of crystal modification B can also be used as a dressing agent for treating seed (fruit, tubers, grains) and plant cuttings to protect them against fungus infections and against phytopathogenic fungi occurring in the soil. It is also effective against insect pests, e.g. against cereal pests, especially rice pests.

Target crops to be protected within the scope of this invention include, for example, the following species of plant: cereals (wheat, barley, rye, oats, rice, maize, sorghum and related species); beets (sugar beet and fodder beet); pomes, stone fruit and berries (apples, pears, plums, peaches, almonds, cherries, strawberries, raspberries and blackberries); leguminous plants (beans, lentils, peas and soybeans); oil plants (rape, mustard, poppy, olives, sunflowers, coconut, castor oil plants, cocoa beans and groundnuts); cucumber plants (marrows, cucumbers and melons); fibre plants (cotton, flax, hemp and jute); citrus fruit (oranges, lemons, grapefruit and mandarins); vegetables (spinach, lettuce, asparagus, cabbages, carrots, onions, tomatoes, potatoes and paprika); lauraceae (avocados, cinnamon and camphor); and plants such as tobacco, nuts, coffee, sugar cane, tea, pepper, vines, hops, bananas and natural rubber plants, as well as ornamentals.

The Examples that follow illustrate the invention in greater detail without, however, limiting it in any way.

PREPARATION EXAMPLES

Example P1

Preparation of (4-cydopropyl-6-methyl-pyrimidin-2-yl)-phenyl-amine 90 kg of phenylguanidine carbonate are suspended in 190 kg of methylcyclohexane, and 63.3 kg of 1-cyclopropyl-1,3-butanedione are added thereto. Then, with stirring for 6 hours at from 100° to 110° C., the water of reaction that forms is removed by azeotropic distillation. The reaction mixture is cooled to from 50° to 60° C., then extraction is carried out with 80 kg of water at pH 3–4 and the aqueous phase is separated off. After the addition of 50 kg of water, extraction is carried out a second time at pH 9–10. The aqueous phase is separated off again and the organic phase is heated under reflux at from 105° to 110° C. in order to remove residual water azeotropically.

The product is isolated either A) in the form of a melt or B) by crystallisation.

A) If (4-cyclopropyl-6-methyl-pyrimidin-2-yl)-phenyl-amine is to be isolated in the form of a melt, the solvent is distilled off completely, for example using a falling film evaporator, under reduced pressure. In a subsequent second step under pressure the product is distilled using a thin-layer evaporator and then supplied to the melt-crystallisation in the form of a hot melt.

B) In order to crystallise the product, the organic solution is cooled to from 37° to 40° C. until crystallization begins. After further cooling, the product is filtered off. The moist filter cake is washed with 80 kg of methylcyclohexane and dried in vacuo at from 45° to 50° C. The dried product can then, if desired, also be melted and likewise supplied to the melt-crystallisation.

Example P2

Preparation of (4-cyclopropyl-6-methyl-pyrimidin-2-yl)-phenyl-amine of Crystal Modification B Having a Melting Point of from 73° to 75° C.

The hot product melt, which is fed in continuously, is cooled in a scraper kettle (volume: 250 litres, filling level: 75%) and maintained at 74° C. Using a special rotary stirring arm that passes close to the kettle wall, which is cooled to 50° C., the crystals that form are scraped off the kettle wall. The resulting melt, which now contains seed crystals, is removed from the kettle continuously and conveyed via a suitable distributing apparatus to a cooled surface for shaping as flakes, pellets etc. When the crystallisation process is complete, (4cyclopropyl-6-methyl-pyrimidin-2-yl)-phenyl-amine in the form of crystal modification B is introduced into the formulation process.

FORMULATION EXAMPLES

Example F1

Wettable Powders

|  | a) | b) | c) |
|---|---|---|---|
| Compound of crystal modification B | 25% | 50% | 75% |
| sodium lignosulfonate | 5% | 5% | — |
| sodium laurylsulfate | 3% | — | 5% |
| sodium diisobutylnaphthalene sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording a wettable powder which can be diluted with water to give suspensions of the desired concentration.

Example F2

Dusts

|  | a) | b) |
|---|---|---|
| Compound of crystal modification B | 5% | 8% |
| talcum | 95% | — |
| kaolin | — | 92% |

A ready-for-use dust is obtained by mixing the active ingredient with the carrier and grinding the mixture in a suitable mill.

Example F3

Extruder Granules

| | |
|---|---|
| Compound of crystal modification B | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air. The resulting granules can be stored indefinitely at low temperatures (−20° C. to +20° C.) as well as at relatively high temperatures (+20° C. to +55° C.).

Example F4

Coated Granules

| | | |
|---|---|---|
| Compound of crystal modification B | | 3% |
| polyethylene glycol (mol. wt. 200) | 3% | |
| kaolin | | 94% |

The finely ground active ingredient is uniformly applied, in a mixer, to the kaolin moistened with polyethylene glycol. Non-dusty coated granules are obtained in this manner.

(mol. wt.=molecular weight)

Example F5

Suspension Concentrate

| | |
|---|---|
| Compound of crystal modification B | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% | 0.8% |
| aqueous emulsion | 0.8% |
| water | 32% |

The finely ground active ingredient is intimately mixed with the adjuvants, giving a suspension concentrate stable to storage at low temperatures and at relatively high temperatures from which suspensions of any desired concentration can be obtained by dilution with water.

APPLICATION EXAMPLES

Example A1

Physico-chemical Behaviour of the Two Crystal Modifications After Prolonged Storage A formulation according to Example F1 c) is prepared from each of crystal modifications A and B and their physico-chemical behaviour is determined. After 6 months' storage at 50° C. that behaviour has not altered in the case of the formulation comprising crystal modification B according to the invention. The suspensibility and dispersibility of the formulation comprising the known crystal modification A, on the other hand, is significantly poorer after 6 months at 22° C. and after one month at 35° C.

The following results are obtained (RT=room temperature).

| Length of storage [months] | 1 | | | | | 3 | | | | | 6 | | | | |
|---|---|---|---|---|---|---|---|---|---|---|---|---|---|---|---|
| Storage temperature [°C.] | −18 | RT | 35 | 40 | 50 | −18 | RT | 35 | 40 | 50 | −18 | RT | 35 | 40 | 50 |
| modification A | | | | | | | | | | | | | | | |
| suspensibility | + | + | /− | − | − | + | + | /− | − | − | + | + | /− | − | − |
| sieve residue | + | + | / | − | − | + | + | / | − | − | + | + | / | − | − |
| modification B | | | | | | | | | | | | | | | |
| suspensibility | + | + | + | + | + | + | + | + | + | + | + | + | + | + | + |
| sieve residue | + | + | + | + | + | + | + | + | + | + | + | + | + | + | + |

Evaluation: +good /satisfactory −poor

Example A2

Action Against *Venturia inaequalis* on Apple Shoots

Apple cuttings with 10–20 cm long fresh shoots are sprayed with a spray mixture (0.006% active ingredient) prepared from a wettable powder formulation of the test compound of modification B having a melting point of from 73° to 75° C. The treated plants are infected 24 hours later with a conidia suspension of the fungus. The plants are then incubated for 5 days at 90–100% relative humidity and placed in a greenhouse for a further 10 days at 20°–24° C. Scab infestation is evaluated 15 days after infection.

(4-Cyclopropyl-6-methyl-pyrimidin-2-yl)-phenyl-amine of crystal modification B reduces Venturia infestation to from 0 to 10%. Untreated and infected control plants, on the other hand, exhibit 100% Venturia infestation.

What is claimed is:

1. (4-Cyclopropyl-6-methyl-pyrimidin-2-yl)-phenyl-amine of crystal modification B of high eutectic purity (content at least 98%) and having a melting point higher than 73° C., preferably from 73° to 75° C., which has an IR spectrum having an NH band at 3200–3300 cm$^{-1}$ and an X-ray powder diagram having the following data

| d-value (Å) | Intensity |
|---|---|
| 12.9 | medium |
| 8.7 | strong |
| 6.8 | strong |
| 6.1 | weak |

-continued

| d-value (Å) | Intensity |
|---|---|
| 5.93 | very weak |
| 5.66 | strong |
| 5.39 | weak |
| 5.19 | very weak |
| 4.96 | weak |
| 4.81 | medium |
| 4.75 | medium |
| 4.55 | very strong |
| 4.47 | medium |
| 4.36 | weak |
| 3.97 | weak |
| 3.86 | medium |
| 3.80 | very strong |
| 3.78 | medium |
| 3.67 | medium |
| 3.56 | medium |
| 3.54 | very weak |
| 3.42 | medium |
| 3.38 | weak |
| 3.30 | medium |
| 3.25 | very weak |
| 3.16 | weak |
| 3.09 | weak |
| 3.04 | very weak. |

2. A process for the preparation of (4-cyclopropyl-6-methyl-pyrimidin-2-yl)-phenyl-amine of crystal modification B according to claim 1, wherein the crystallisation is carried out at a temperature higher than 26° C.

3. A process according to claim 2, wherein the crystallisation is carried out in the presence of a solubiliser.

4. A process according to claim 3, wherein an organic solvent is used as solubiliser.

5. A process according to claim 4, wherein toluene, isopropanol or methylcyclohexane is used as solubiliser.

6. A process for the preparation of (4-cyclopropyl-6-methyl-pyrimidin-2-yl)-phenyl-amine of crystal modification B according to claim 1, wherein that compound is obtained by melt-crystallisation.

7. A process according to claim 6, wherein the preparation is carried out in a scraper kettle.

8. A process according to claim 6, wherein the crystals that form are scraped off the cooled kettle wall.

9. A process according to claim 8, wherein the kettle wall is at a temperature of from 40° C. to 60° C.

10. A process according to claim 9, wherein the temperature is 50° C.

11. A process according to claim 6, wherein in the melt-crystallisation first of all a melt containing seed crystals is produced.

12. A process according to claim 6, wherein in order to complete the crystallisation process the melt is cooled further.

13. A fungicidal composition comprising as active ingredient (4-cyclopropyl-6-methyl-pyrimidin-2-yl)-phenyl-amine of crystal modification B having a melting point higher than 73° C. in a fungicidally effective amount, together with a suitable carrier.

14. A process for the preparation of a composition according to claim 13, which comprises intimately mixing (4-cyclopropyl-6-methyl-pyrimidin-2-yl)-phenyl-amine of crystal modification B having a melting point higher than 73° C. with a suitable solid or liquid adjuvant and/or surfactant.

15. A process for the preparation of a composition according to claim 14, which comprises passing a melt containing seed crystals of (4cyclopropyl-6-methyl-pyrimidin-2-yl)-phenyl-amine of crystal modification B having a melting point higher than 73° C., using a suitable distributing apparatus, to a cooled surface, from which the crystallised active ingredient is preferably introduced directly into a formulation apparatus suitable for the particular purpose.

16. A method of controlling or preventing fungus infestation in cultivated plants, which comprises the application to the plant, to parts of the plant or to the locus thereof, as active ingredient, (4-cyclopropyl-6-methyl-pyrimidin-2-yl)-phenyl-amine of crystal modification B having a melting point higher than 73° C.

17. A method according to claim 16, wherein the parts of the plant are the seed.

* * * * *